United States Patent [19]
Fukuda et al.

[11] Patent Number: 5,260,764
[45] Date of Patent: Nov. 9, 1993

[54] OPTICAL PARTICLE ANALYZING APPARATUS HAVING TWO TYPES OF LIGHT SOURCE

[75] Inventors: Masakazu Fukuda; Hiroyuki Nakamoto; Hiroyuki Seshimo; Hidemichi Tohori, all of Hyogo, Japan

[73] Assignee: Toa Medical Electronics Co., Ltd., Kobe, Japan

[21] Appl. No.: 530,102

[22] Filed: May 29, 1990

[30] Foreign Application Priority Data

Feb. 8, 1990 [JP] Japan ................... 2-29052

[51] Int. Cl.⁵ .............. G01N 21/00; G01N 15/14
[52] U.S. Cl. .................. 356/73; 250/458.1; 250/461.2; 356/39; 356/318; 356/336
[58] Field of Search .............. 356/73, 39, 72, 317, 356/318, 417, 336; 250/458.1, 459.1, 461.1, 461.2

[56] References Cited

U.S. PATENT DOCUMENTS

| | | | |
|---|---|---|---|
| 3,824,402 | 7/1974 | Mullaney et al. | 250/565 |
| 4,284,355 | 8/1981 | Hansen et al. | 356/335 |
| 4,325,706 | 4/1982 | Gershman et al. | 356/39 |
| 4,599,307 | 7/1986 | Saunders et al. | 356/39 |
| 4,730,922 | 3/1988 | Bach et al. | 356/73 |
| 4,842,406 | 6/1989 | Von Bargen | 356/336 |

FOREIGN PATENT DOCUMENTS

| | | | |
|---|---|---|---|
| 0022670 | 1/1981 | European Pat. Off. | 33/50 |
| 0193356 | 9/1986 | European Pat. Off. | |
| 60-260830 | 12/1985 | Japan. | |
| 61-280565 | 12/1986 | Japan. | |
| 62-34058 | 2/1987 | Japan. | |
| 64-35366 | 2/1989 | Japan. | |

OTHER PUBLICATIONS

Steinkamp, John A. (Flow Cytometry), Review of Scientific Instruments, vol. 55, No. 9, Sep. 1984.

Primary Examiner—Vincent P. McGraw
Assistant Examiner—K. P. Hantis
Attorney, Agent, or Firm—Fitch, Even, Tabin & Flannery

[57] ABSTRACT

An optical particle analyzing apparatus includes a flow cytometer in which laser light and lamp light having a wavelength shorter than that of the laser light are used simultaneously when particles in a blood specimen or the like are analyzed by the flow cytometer. Scattered light emitted by a particle due to irradiation with the laser light and fluorescence emitted by the particle due to irradiation with the lamp light are detected. A signal indicative of the scattered light is used as a timing signal to detect the fluorescence. This arrangement makes it possible to reduce the size and cost of the apparatus.

8 Claims, 5 Drawing Sheets

LASER LIGHT

LAMP LIGHT 5,260,764

OPTICAL PARTICLE ANALYZING APPARATUS HAVING TWO TYPES OF LIGHT SOURCE

BACKGROUND OF THE INVENTION

1. Field of the Invention

This invention relates to an optical particle analyzing apparatus for irradiating with light a flow of particles in a specimen such as cells suspended in a liquid, detecting scattered light or fluorescence emitted by individual particles, and classifying and enumerating the cells. More particularly, the invention relates to an optical particle analyzing apparatus employing both a laser light source and a lamp light source as the irradiating light sources.

2. Description of the Prior Art

The classification and enumeration of particles such as white blood cells or reticulocytes contained in blood is a necessary and useful tool in clinical analysis, and the trend recently is to use an automatic particle analyzing apparatus for this purpose. In an analyzing apparatus of this kind, a blood specimen is drawn up from a specimen suction unit, the specimen is pretreated automatically within the apparatus and delivered to a detector, and signals detected by the detector are counted and analyzed to obtain an output of the number and content of prescribed cells. One example of such an apparatus is a flow cytometer, in which the blood specimen is diluted and stained to obtain a specimen solution that is then passed through the central portion of a flow cell in the form of a fine stream. A detecting zone is formed by irradiating a portion of the fine stream with a narrow beam of light from a light source, and a change in scattered light or fluorescence generated whenever individual blood cells pass through the detecting zone is detected by a photodetector. By way of example, a two-dimensional distribution, in which scattered light intensity and fluorescent light intensity are plotted along two axes, is formed from the detected signals, and each of the particles is classified and counted by setting demarcation lines in the two-dimensional distribution. For example, reticulocytes are demarcated from mature red blood cells or platelets and the number or ratio of the reticulocytes is obtained. An argon laser often is used as the light source.

In the conventional flow cytometer, the argon laser is used as a light source for exciting particles to fluorescence. The reason for this is that light in the blue region and having a comparatively short wavelength is required to be used as the excitation light in order to produce fluorescence. However, an argon laser is high in cost, and not only does the laser itself occupy a large amount of space, but the peripheral equipment for the laser such as the power supply for driving the laser, also is large in size. Another problem is that a large amount of power is consumed overall.

Though it is preferred to use small-size, inexpensive light-source equipment instead of an argon laser for the purpose of producing fluorescence, a semiconductor laser capable of emitting light in the blue region is not available at the present time. Of course there are semiconductor lasers which produce light in the red through infrared regions, but fluorescence cannot be obtained with light sources that operate in these wavelength regions.

SUMMARY OF THE INVENTION

Accordingly, an object of the present invention is to provide an optical particle analyzing apparatus which uses a flow cytometer, wherein smaller size and lower cost can be achieved by improving the light-source equipment.

According to the present invention, the foregoing object is attained by providing an optical particle analyzing apparatus in which a large-size, costly light source such as an argon laser is not used as the light source for exciting particles in a specimen to fluorescence, but rather in which use is made of small-size, readily available and easily maintained lamp-type light-source device such as a halogen lamp, mercury-arc lamp or tungsten lamp.

More specifically, the foregoing object is attained by providing an optical particle analyzing apparatus for classifying and enumerating particles, comprising a flow cell, means for passing particles such as cells stained with a fluorescent stain through the flow cell in the form of a fine particle stream, means for irradiating an irradiating zone in the fine stream of particles with two types of light, means for detecting respective ones of scattered light and fluorescence produced by the particles in the zone, and means for processing and analyzing signals out-putted by the detecting means, wherein the two kinds of light which irradiate the irradiating zone are a laser light beam, emitted by a laser light source and a lamp light beam, which has a wavelength shorter than that of the laser light beam, emitted by a lamp light source, the laser light beam and lamp light beam intersect each other at the irradiating zone to irradiate the same, the irradiating laser light beam is narrowed to a beam narrower than the lamp light beam in a direction in which the particles flow, there is provided a signal processor for signal-processing a scattered-light signal, which results from the laser light beam and is detected in the irradiating zone, and a fluorescence signal, which results from the lamp light beam and is detected in the irradiating zone, and when the fluorescence signal is signal-processed by the signal processor, the scattered-light signal is used as a timing signal for this signal processing.

In a preferred embodiment, the laser light source is a semiconductor laser.

Further, the optical particle analyzing apparatus of the present invention is characterized in that the irradiating light beams composed of the laser light beam and lamp light beam intersect each other at an angle of approximately 90°, and forward-scattered light and side fluorescence, which result from the laser light beam and lamp light beam, respectively, and are emitted in the same direction, are detected upon undergoing wavelength selection.

The apparatus is further characterized in that the irradiating light beams composed of the laser light beam and lamp light beam intersect each other at an angle of approximately 90°, and forward-scattered light, which results from the laser light beam and is emitted in a first direction, as well as side-scattered light and back fluorescence, which result from the laser light beam and lamp light beam, respectively, and are emitted in a section direction, are detected.

Though a lamp light source generally is small in size and low in cost, the irradiating zone in the flow cytometer through which the specimen containing the suspended particles flows cannot be irradiated with light from the lamp light source that is as intense as that from an argon laser. However, light from a lamp has considerable width, meaning that it is not a single spectrum but spreads over a wide wavelength region. Such light contains light corresponding to a region having a high absorption spectrum intensity specific to particles. Consequently, lamp light is readily absorbed by particles even though the intensity of the light is not as strong as that of laser light, and fluorescence having a light intensity equivalent to that achieved with laser light can be obtained even when lamp light is employed.

Further, it is difficult for lamp light to provide a narrow beam free of an irregular light intensity distribution, as in the manner of laser light, and as a result the fluorescence signal with a broad width. On the basis of such a signal, it is difficult to detect a characteristic quantity for every particle derived from the amount of fluorescence. For example, detecting the peak of the signal and obtaining its value is impossible without complicated signal processing. On the other hand, the scattered-light signal resulting from the laser light is a signal with a single peak. In the present invention, a signal processor is used to detect the value of the fluorescence signal at the moment the scattered-light signal, which results from the laser light, peaks. More specifically, the scattered-light signal is used as a timing signal for the processing of the fluorescence signal. In addition, the peak value of the scattered-light signal also is detected by the signal processor. The scattered light contains side-scattered light and forward-scattered light. Side-scattered light is well suited for obtaining information related to internal morphology such as particle size, and forward-scattered light is suited for obtaining information related to internal morphology such as particle nucleus. In a case where particles such as reticulocytes are independently classified and quantified, it will suffice to detect a forward-scattered light signal and the fluorescence signal. When classifying and quantifying leukocytes, it is necessary to detect a forward-scattered light signal, side-scattered light signal and fluorescence signal.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Figure 1:
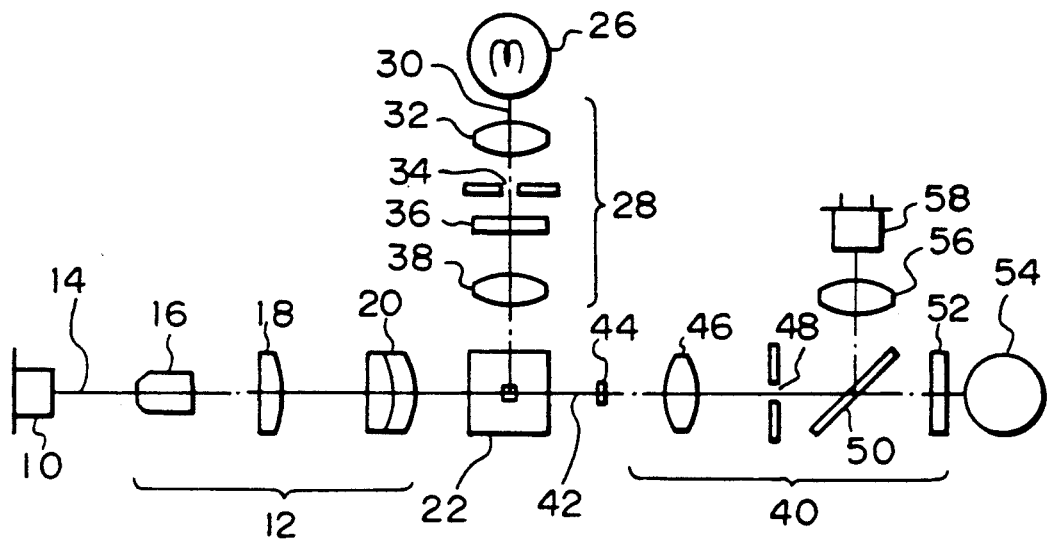
FIG. 1 is a diagram showing the basic construction of an embodiment of a particle analyzing apparatus according to the present invention.
Figure 2:
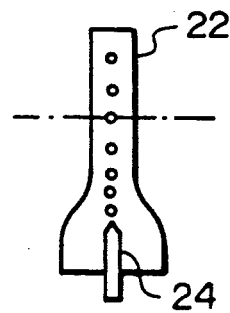
FIG. 2 is a schematic side view showing a flow cell in the apparatus of FIG. 1.

FIG. 1 is a diagram showing the basic construction of an embodiment of a particle analyzing apparatus according to the present invention, and FIG. 2 is a schematic side view showing a flow cell in the apparatus of FIG. 1. The apparatus is capable of classifying and counting various cells, such as reticulocytes, in various specimens, such as blood. By mixing the blood specimen with a reagent containing Oramine-O, the RNA contained in the reticulocytes can be fluorescently stained. This is described in detail in the specifications of Japanese Patent Application Laid-Open (KOKAI) Nos. 61-280565, 62-34058 and 64-35366. The fluorescently stained blood specimen can be discharged from a nozzle 24 at a constant flow rate. A sheathed flow is produced by passing a sheath solution over the periphery of the nozzle 24, and the blood cells are passed in an ordered flow through a narrow irradiating zone at the central portion of the flow cell 22 (the flow is from the back to the front of the page in FIG. 1 and from bottom to top in FIG. 2). A light source 10 is a small-size semiconductor laser which emits red light having a wavelength of 670 nm, by way of example. The light used may be near-infrared light if desired. Numeral 26 denotes a lamp light source such as a halogen lamp. The laser light from the laser 10 is condensed by an irradiating optical system 12, and the light from the lamp 26 is condensed with regard to a selected wavelength thereof by an irradiating optical system 28. The specimen irradiating zone of the flow cell 22 is thus irradiated with the condensed laser light and condensed lamp light. In this embodiment, the flow cell 22 is irradiated with the laser light from the front side of the cell and with the lamp light from one side of the cell. These two irradiating light beams perpendicularly intersect each other at the sheathed flow irradiating zone. Scattered light and fluorescence are produced by passing the fluorescently stained blood cells through the irradiating zone where the light beams intersect each other. In this embodiment, forward-scattered light obtained by using the laser light as the irradiating light is emitted over a narrow angle of 5°–15° with respect to an optic axis 14 of laser irradiation, side fluorescence obtained by using the lamp light as excitation light is emitted at an angle of about 90° with respect to an optic axis 30 of lamp-light irradiation, the forward-scattered light and side fluorescence undergo wavelength selection executed by a light-receiving optical system 40, and these are then detected by respective light-receiving elements 58, 54.

Figure 3:
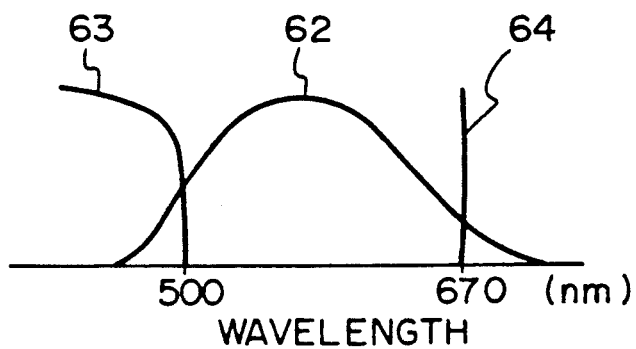
FIG. 3 is a characteristic diagram of irradiation.

FIG. 3 is a diagram showing typical characteristics of irradiating light, in which numerals 63, 62, 64 respectively denote characteristic curves of excitation light (lamp light), fluorescence and irradiating light (laser light) in order starting from the shorter wavelengths.

The optical system 12 of the laser light comprises a collimator lens 16 and condenser lenses 18, 20, and the optical system 28 of the lamp light comprises a condenser lens 32, a pin hole 34, a filter 36 and a condenser lens 38.

Figure 4A:
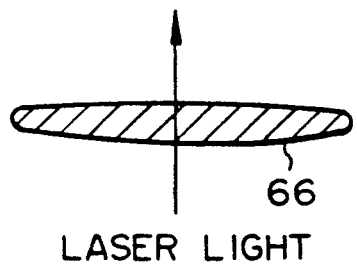
FIG. 4a shows a cross section of laser light irradiation and FIG. 4b is a distribution of the light intensity thereof.
Figure 5A:
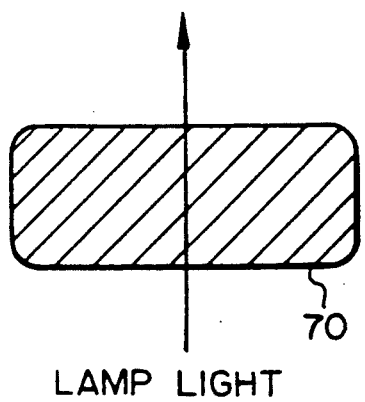
FIG. 5a shows a cross section of lamp light irradiation.

FIGS. 4a and 5a are cross sections or irradiating light in the specimen irradiating zone as seen from the downstream side of the laser-light optic axis 14 and the downstream side of the lamp-light optic axis 30, repsectively.

Figure 4B:
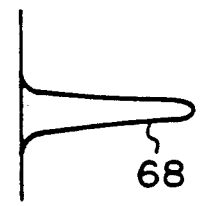
Figure 5B:
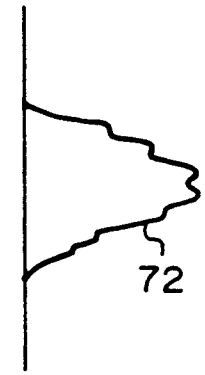
FIG. 5b is a distribution of the light intensity thereof.

The arrows indicate the direction of specimen flow. As shown in FIG. 4a, the spread of a laser beam 66 is narrowed, in the direction of specimen flow, to a value approximately equivalent to the particle diameter of the blood cell, e.g., about 10 μm. Spread in the direction perpendicular to the specimen flow direction and the direction of the irradiation optic axis is made sufficiently greater than the blood cell particle diameter, e.g., 150–300 μm. Thus, the cross section of laser beam 66 is elliptical in shape. As shown in FIG. 4b, the light intensity distribution 68 of this laser beam is a Gaussian distribution having a single peak. As shown in FIG. 5a, the cross section of a lamp light beam 70 in the irradiating zone of the sheathed flow is difficult to be narrowed down in the manner of the laser beam 66, and the light intensity distribution 72 of the lamp light beam is irregular, as shown in FIG. 5b. Whenever a fluorescently stained blood cell particle passes through the irradiating zone at the intersection of these light beams, the particle emits scattered light and fluorescence. By detecting and analyzing the scattered light and fluorescence, such information as particle size and RNA content can be obtained with regard to each individual blood cell particle.

In the description of this embodiment, unless specified otherwise, "forward-scattered light" shall mean forward-scattered light resulting from the laser light, "side-scattered light" shall mean side-scattered light resulting from the lamp light, and "side fluorescence" shall mean side fluorescence resulting from the lamp light.

The light emitted from the blood cell particles, namely the forward-scattered light resulting from the laser light, and the side-scattered light and side fluorescence resulting from the lamp light, undergoes wavelength selection executed by the light-receiving optical system 40, and the forward-scattered light and side fluorescence are detected by the light-receiving elements 58, 54, respectively. In this case, as shown in FIG. 1, the light-receiving optical system 40 comprises a collector lens 46, a pin hole 48, a dichroic mirror 50, a band-pass filter 52 and a collector lens 56. The dichroic mirror 50 is arranged at an angle of 45° with respect to the light-receiving optic axis 42 and has a characteristic in accordance with which 80–90% of short-wavelength light is passed (i.e., 10–20% is reflected) and more than 99% of long-wavelength light is reflected (i.e., less than 15 is passed) with regard to the light received by the mirror. Consequently, more than 99% of the forward-scattered light resulting from the laser light is reflected to impinge upon the light-receiving element 58. The forward-scattered light that is transmitted by the dichroic mirror 50 is less than 1%. Medium- and short-wavelength light is transmitted by the dichroic mirror 50 at a damping factor of 10–20%. The medium-wavelength light, namely the side fluorescence resulting from the lamp light, is selectively transmitted by the band-pass filter 52 to impinge upon the light-receiving element 54. The short-wavelength light, namely the side-scattered light resulting from the lamp light, has an intensity which is less than 1% that of the forward-scattered light resulting from the laser light. This short-wavelength light is sufficiently attenuated by the band-pass filter 52. The slight amount of forward-scattered light transmitted by the dichroic mirror 50 is also sufficiently attenuated by the band-pass filter 52. Thus, the side fluorescence can be detected by the light-receiving element 54 without being influenced by the forward-scattered light and side-scattered light. On the other hand, 10–20% of the medium- and short-wavelength side-scattered light and side fluorescence is reflected, after which the remaining light impinges upon the light-receiving element 58. However, since this light is very weak in comparison with the forward-scattered light, it has no effect upon detection of the forward-scattered light. A photodiode and photomultiplier are suitable as the light-receiving elements 58, 54, respectively.

In a case where lamp light is used for exciting fluorescence, light as strong as the light from an argon laser is not obtained. However, as shown in FIG. 3, the light is not of a single wavelength and has components of wavelengths shorter than that of an argon laser.

Figure 6:
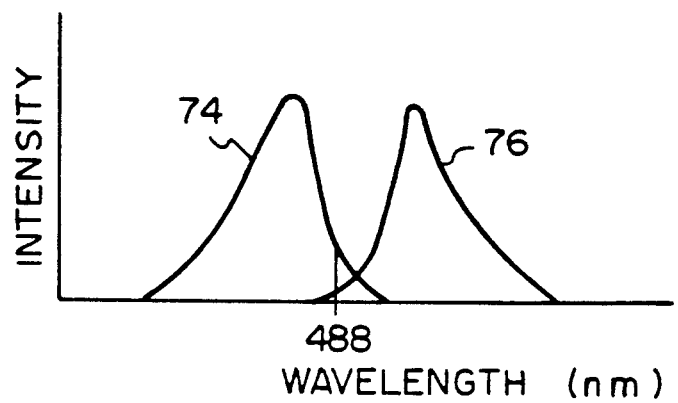
FIG. 6 is a particle light-absorption and fluorescence spectrum characteristic diagram.

FIG. 6 illustrates a light absorption/fluorescence spectrum for blood cell particles. When an argon laser wavelength of 488 nm is situated on the right-hand skirt of an absorption spectrum 74, the intensity of the absorption spectrum in this wavelength region is low. Therefore, in order to obtain strong fluoescence, irradiation is necessary with light which is correspondingly strong. However, since the absorption spectrum 74 has a high intensity, light having a wavelength shorter than 488 nm is readily absorbed and strong fluorescence is produced even with weak light. Thus, fluorescence approximately equivalent to that achievable with an argon laser is obtained even with the comparatively weak light provided by lamp light. Accordingly, no impediment is encountered in terms of detecting fluorescence. numeral 76 denotes a fluorescence spectrum corresponding to the absorption of light by blood cell particles.

As shown in FIGS. 4a and 4b, the laser light beam can be narrowed in the direction of particle flow, and the light intensity distribution thereof is a Gaussian distribution. Accordingly, when the blood cell particles pass through the irradiating zone, a pulse-shaped forward-scattered light signal 78 having a single peak is obtained. The crest value of this scattered-light signal corresponds to the size of the particle which has passed through the irradiating zone.

Figure 7:
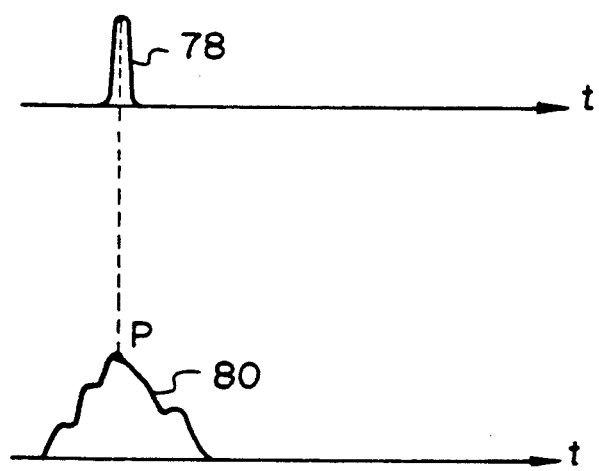
FIG. 7 is a view for describing a scattered-light signal and fluorescence signal.

On the other hand, as shown in FIGS. 5a and 5b, the lamp light beam has a light spectrum width of considerable size, and the distribution is highly irregular. Consequently, the obtained fluorescence signal 80 also is large in width and irregular, as illustrated in FIG. 7. It is difficult to extract the intensity of fluorescence from such a signal. Accordingly, in the present invention, the forward-scattered light signal 78 is used as the trigger signal of the side fluorescence signal in signal processing. In other words, crest value P of the fluorescence signal at the moment the scattered-light signal peaks is detected as the intensity of fluorescence.

Figure 8:
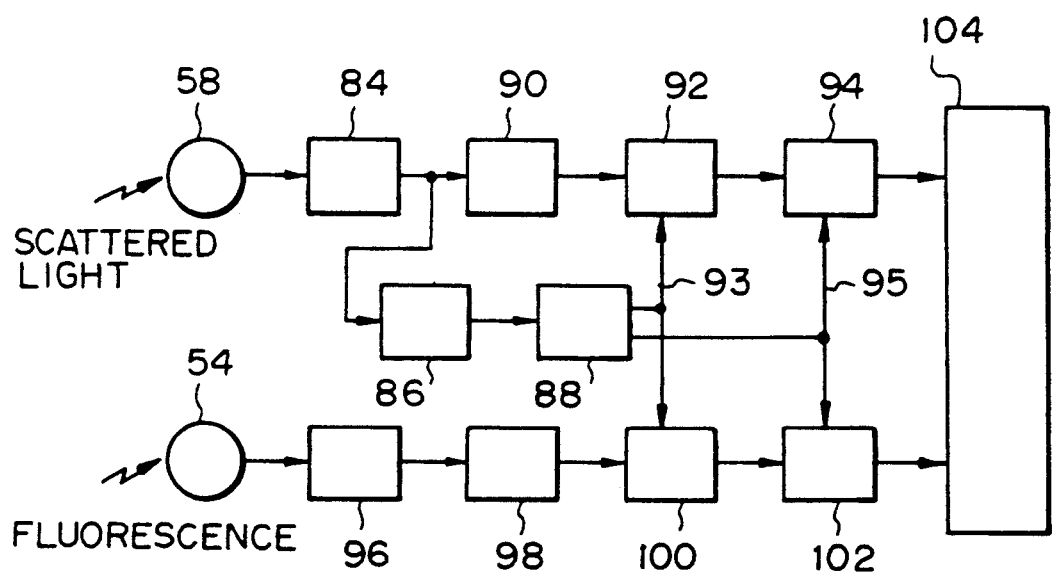
FIG. 8 is a block diagram showing an example of a signal processor.

FIG. 8 is a block diagram showing an example of a signal processor 82. Forward-scattered light is subjected to a photoelectric conversion by the light-receiving element 58, the output of which is amplified by an amplifier circuit 84. The amplified signal is detected from the leading edge to the peak thereof by a peak detecting circuit 86. The latter can readily be constructed using a differentiating circuit and a comparator, by way of example. The amplified signal from the amplifier circuit 84 is fed into a phase compensating circuit 90, where a predetermined time delay is applied to the signal. A discriminating circuit 88 determines whether the detection signal from the peak detecting circuit 86 is a signal indicative of a blood cell or noise.

This can be judged by the width of the scattered-light signal. The output of the phase compensating circuit 90 is applied to a peak-hold circuit 92, whose output is delivered to an A/D converter circuit 94. If the signal from the peak detecting circuit 86 is judged to be a blood-cell signal, the discriminating circuit 88 sends a setting signal 93 to the peak-hold circuit 92 which responds by holding the peak value of the blood-cell signal. In addition, the discriminating circuit 88 sends and A/D conversion starting signal to the A/D converter 94 which responds by performing an A/D conversion. As a result, the peak value of the forward-scattered light signal indicative of a blood cell particle is converted from an analog to a digital quantity.

Meanwhile, the side fluorescence is subjected to a photoelectric conversion by the light-receiving element 54. The resulting signal is amplified by an amplifier circuit 96, and the amplified signal is delivered to a phase compensating circuit 98. This signal is subjected to peak-hold and A/D conversion processing by a peak-hold circuit 100 and and A/D converter circuit 102, respectively, at a timing identical with that of the fluorescence signal. The peak value of the scattered-light signal and the peak value of the fluorescence signal which prevails when the scattered-light signal is peak are delivered to a data analyzing unit 104, where analysis of various kinds is performed based on the value of the intensity of fluorescence, etc.

Figure 9:
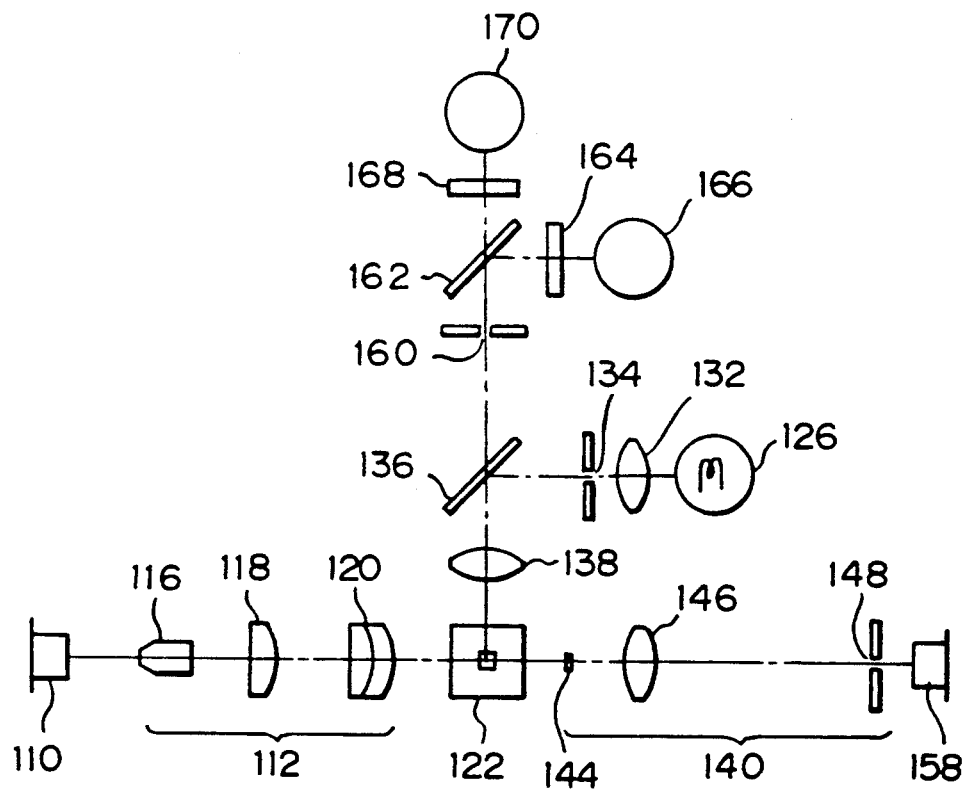
FIG. 9 is a diagram showing the basic construction of a second embodiment of a particle analyzing apparatus according to the present invention.

FIG. 9 is a diagram showing the basic construction of another embodiment of the present invention. In this arrangement, forward-scattered light emitted by particles in the irradiating zone owing to irradiation with laser light from a laser light source 110 is detected by a light-receiving element 158, side-scattered light which is similarly emitted and is detected by a light-receiving element 166, and back fluorescence emitted by particles owing to irradiation with lamp light from a lamp light source 126 is detected by a light-receiving element 170. Since it is arranged to detect the side-scattered light as well, highly precise analysis of particles can also be performed. For example, this arrangement is suitable for classifying and counting leukocytes contained in blood cell particles.

Owing to the action of an irradiating optical system comprising a lens 132, a pin hole 134, a dichroic mirror 136 and a lens 138, the specimen irradiating zone of a flow cell 122 is irradiated solely with the shortwave light of the light emitted by the lamp light source 126. Meanwhile, the specimen irradiating zone is irradiated with laser light, emitted by the laser light source 110, by means of an irradiating optical system comprising lenses 116, 118, 120. The resulting forward-scattered light is gathered by a light-receiving optical system 140 comprising a beam splitter 144, a lens 146 and a pin hole 148, and the gathered light is detected by the light-receiving element 158. In addition, the side-scattered light resulting from the laser light, as well as the back-scattered light and back fluorescence resulting from the lamp light, undergoes wavelength selection executed by a light-receiving optical system comprising a lens 138, a dichroic mirror 136, a pin hole 160, a dichroic mirror 162 and filters 164, 168, and the side-scattered light resulting from the laser light and back fluorescence resulting from the lamp light are detected by light-receiving elements 166, 170, respectively.

Thus, the optical particle analyzing apparatus of the present invention uses lamp light for exciting specimen particles to fluorescence, uses a semiconductor laser for scattered-light illumination, and is so arranged that the laser light beam and lamp light beam from compact, low-cost light sources intersect each other at the fine particle stream irradiating zone of a flow cell to irradiate the particles. As a result, the scattered light and fluorescence from one particle can be detected at the same location and at the same timing. In addition, since the laser light can be finely narrowed and possesses a single peak, the scattered-light signal also will be a single-peak signal. Since the scattered-light signal is used as a timing signal to detect the value of the fluorescence signal, it is possible to detect the fluorescence signal, which is correlated with the amount of fluorescence emitted by the particle, even if the distribution of the lamp light intensity is irregular.

In a case where the forward-scattered light resulting from the laser light and the fluorescence resulting from the lamp light are detected in an identical direction, classification and enumeration of reticulocytes can be performed with a simple optical system.

Analysis with even greater precision is made possible by detecting forward-scattered light which results from the laser light and is emitted in a first direction, as well as side-scattered light and back fluorescence which result from the laser light and lamp light, respectively, and are emitted in a second direction. Such an arrangement is well suited to the classification and enumeration of leukocytes.

As many apparently widely different embodiments of the present invention can be made without departing from a spirit and scope thereof, it is to be understood that the invention is not limited to the specific embodiments thereof except as defined in the appended claims.

What is claimed is:

1. An optical particle analyzing apparatus for classifying and enumerating particles, comprising:
   a flow cell;
   means for passing a fine stream of cells stained with a fluorescent stain through said flow cell;
   means for continuously irradiating an irradiating zone in the fine stream of cells in said flow cell with two kinds of light;
   means for detecting respective ones of forward scattered light and fluorescence produced by the cells in the irradiating zone;
   means for processing and analyzing signals outputted by said detecting means, wherein said two kinds of light which irradiate the irradiating zone are a laser light beam emitted by a semiconductor laser light source and a lamp light beam, which has a wavelength shorter than that of the laser light beam, emitted by a lamp light source, the laser light beam and lamp light beam intersect each other at the irradiating zone to irradiate the same, and the irradiating laser light beam is narrowed to a beam narrower than the lamp light beam in a direction in which the cells flow; and
   a signal processor for signal-processing a forward scattered-light signal which results from the laser light beam and is detected in the irradiating zone, and a fluorescence signal which results from the lamp light beam and is detected in the irradiating zone, wherein when the fluorescence signal is signal-processed by said signal processor, the forward scattered-light signal is used as a timing signal for this signal processing so that the value of the fluorescence signal at the moment the scattered-light signal peaks is taken as the intensity of fluorescence.

2. The apparatus according to claim 1, wherein the irradiating light beams composed of the laser light beam and lamp light beam intersect each other at an angle of approximately 90°, and forward-scattered light and side fluorescence which result from the laser light beam and lamp light beam, respectively, and are emitted in the same direction, are detected upon undergoing wavelength selection.

3. The apparatus according to claim 1, wherein the irradiating light beams composed of the laser light beam and lamp light beam intersect each other at an angle of approximately 90°, and forward-scattered light which results from the laser light beam and is emitted in a first direction, as well as side-scattered light and back fluorescence which result from the laser light beam and lamp light beam, respectively, and are emitted in a second direction, is detected.

4. An optical analyzer for classifying and enumerating cells, comprising:
a flow cell having an irradiating zone through which a stream of cells stained with a fluorescent stain flows;
a semiconducting laser for generating a laser beam which irradiates said stream of cells at said irradiating zone of said flow cell;
an optical energy source for generating a light beam having a wavelength shorter than the wavelength of said laser beam which continuously irradiates said stream of cells at said irradiating zone of said flow cell and intersects said laser beam at said irradiating zone of said flow cell, whereby said stained cells fluoresce when irradiated by said light beam;
a condensing lens system receiving said laser beam for narrowing said laser beam narrower than said light beam in the direction in which said stream of cells flow;
a signal processor which detects the interaction of said laser and light beams with said stream of cells for generating a first signal corresponding to the irradiation of said stream of cells by said laser and a second signal corresponding to the fluorescence resulting from the irradiation of said stream of cells by said light beam; and
a data processor coupled to said signal processor for processing and analyzing said second signal generated at the same time said first signal is generated.

5. The optical analyzer of claim 4 wherein said laser and light beams intersect at an angle of approximately ninety degrees.

6. The optical analyzer of claim 4 wherein
said irradiation of said stream of cells by said laser beam produces forward scattered light;
said irradiation of said stream of cells by said light source produces side fluorescence emitted in the same direction as said forward scattered light; and
said signal processor uses wavelength detection to differentiate between said forward scattered light and said side fluorescence.

7. An optical analyzer for classifying and enumerating cells, comprising:
a flow cell having an irradiating zone through which a stream of cells stained with a fluorescent stain flows;
a semiconducting laser for generating a laser beam which irradiates said stream of cells at said irradiating zone of said flow cell to produce forward scattered light which is emitted in a first direction and to produce side scattered light which is emitted in a second direction;
an optical energy source for generating a light beam having a wavelength shorter than the wavelength of said laser beam which continuously irradiates said stream of cells at said irradiating zone of said flow cell and intersects said laser beam at said irradiating zone of said flow cell to produce back fluorescence emitted in said second direction;
a condensing lens system receiving said laser beam for narrowing said laser beam narrower than said light beam in the direction in which said stream of cells flow;
a signal processor which detects said forward scattered light, side scattered light, and back fluorescence and generates a first signal corresponding to said forward scattered light, a second signal corresponding to said side scattered light, and a third signal corresponding to said back fluorescence;
a data processor coupled to said signal processor for processing and analyzing said second and third signals generated at the same time said first signal is generated.

8. The optical analyzer of claim 7 wherein said signal processor uses wavelength detection to differentiate between said forward scattered light, side scattered light, and back fluorescence.

* * * * *

UNITED STATES PATENT AND TRADEMARK OFFICE
CERTIFICATE OF CORRECTION

PATENT NO. : 5,260,764
DATED : November 9, 1993
INVENTOR(S) : Fukuda, et al.

It is certified that error appears in the above-indentified patent and that said Letters Patent is hereby corrected as shown below:

ON THE TITLE PAGE:

[30] Change "2-29052" to --29052--.

Signed and Sealed this

Twelfth Day of July, 1994

Attest:

BRUCE LEHMAN

*Attesting Officer*    Commissioner of Patents and Trademarks